(12) United States Patent
Campbell

(10) Patent No.: US 6,485,431 B1
(45) Date of Patent: Nov. 26, 2002

(54) METHOD AND APPARATUS FOR DETERMINING CARDIAC OUTPUT OR TOTAL PERIPHERAL RESISTANCE

(75) Inventor: Duncan Campbell, Beecroft (AU)

(73) Assignee: Duncan Campbell Patents Pty. Ltd., Beecroft (AU)

( * ) Notice: Subject to any disclaimer, the term of this patent is extended or adjusted under 35 U.S.C. 154(b) by 5 days.

(21) Appl. No.: 09/714,721

(22) Filed: Nov. 16, 2000

(30) Foreign Application Priority Data

Nov. 24, 1999 (AU) .............................................. PQ4205

(51) Int. Cl.$^7$ ................................................ A61B 5/00
(52) U.S. Cl. ........................ 600/526; 600/500; 600/505
(58) Field of Search ................................ 600/485, 500, 600/504, 505, 526

(56) References Cited

U.S. PATENT DOCUMENTS

| | | | | |
|---|---|---|---|---|
| 5,101,828 A | * | 4/1992 | Welkowitz et al. ......... | 600/500 |
| 5,183,051 A | * | 2/1993 | Kraidin et al. ............... | 600/500 |
| 5,400,793 A | * | 3/1995 | Wesseling .................... | 600/500 |
| 5,423,322 A | * | 6/1995 | Clark .......................... | 600/500 |
| 5,535,753 A | * | 7/1996 | Petrucelli et al. ........... | 600/500 |

\* cited by examiner

Primary Examiner—Robert L. Nasser
(74) Attorney, Agent, or Firm—Edwin D. Schindler

(57) ABSTRACT

A method and apparatus determines continuously mean cardiac output by measuring the arterial pressure e.g. at a finger and calculating therefrom the mean arterial pressure and the time constant of the arterial system (in diastole). Compliance values are provided from a table. Mean cardiac output is then the product of mean arterial pressure and compliance divided by the time constant. Changes in cardiac output can be used for diagnostic purposes. A pressure cuff or pressure tonometer can be used to measure the arterial pressure with a microcomputer providing the necessary calculations.

25 Claims, 3 Drawing Sheets

METHOD AND APPARATUS FOR DETERMINING CARDIAC OUTPUT OR TOTAL PERIPHERAL RESISTANCE

FIELD OF THE INVENTION

The present invention relates to a method for determining cardiac output or total peripheral resistance from the measurement of an arterial pressure waveform and in particular from a non invasive measurement of peripheral circulation.

While it is preferred to use a non-invasive technique to measure the arterial pressure waveform, an invasive technique such as the use of an intra-arterial catheter can also be used. While such a technique is more accurate its use is more restricted to qualified personnel and has more limited use.

BACKGROUND OF THE INVENTION

Intra arterial catheters are in common use during major surgery. These are commonly attached to pressure transducers and the electrical signal is processed to display the pressure waveform as a trace on a visual display monitor. The display indicates systolic, diastolic, mean arterial pressure and heart rate.

At present the most reliable and accepted method of measuring cardiac output for surgical patients derives the cardiac output from a thermodilution technique using the insertion of a pulmonary artery catheter. The procedure is potentially dangerous as the catheter must be passed through the right heart for correct placement. In children it is considered that the danger of the technique outweighs any benefits from the information received.

In each of U.S. Pat. No. 5,535,753 (Petrucelli et al) and U.S. Pat. No. 5,647,369 (Petrucelli et al), a non-invasive technique measures cardiac output using an unmodified Windkessel circuit model representing arterial compliance as a single lumped capacitance. In U.S. Pat. No. 5,535,753 cardiac output is calculated from the mean flow in diastole multiplied by the heart rate with mean flow determined by RMS averaging systolic "current" over the diastolic period. Systolic current is calculated from a model using a LC charge pump circuit for the systolic portion of the cardiac cycle. In U.S. Pat. No. 5,647,369 (Petrucelli et al) provide an allegedly improved measure of cardiac output in a known equation involving a function of pulse pressure, heart rate and compliance. by representing compliance as a function of pulse pressure, age, height and/or weight.

In U.S. Pat. No. 5,836,884 (Chio), cardiac output or peripheral resistance is calculated from a non-invasive cuff pressure method measuring systolic, diastolic and mean arterial pressure and employing formulae using diastolic flow velocity calculated from determinants of the pressure waveform.

Non invasive techniques for determining cardiac output include Doppler ultrasonography using an oesophageal probe and echo cardiography using a probe on the chest wall. The equipment for these techniques is bulky, expensive and unsuited to routine theater use where space is of a limited nature especially during major surgery.

Other techniques for measuring cardiac output use expired gas analysis using a variety of gases. Most of these techniques are experimental only and have not been accepted for general clinical use.

Another form of measurement involves a dye dilution technique but it is of limited use as it does not allow frequent repeated measurement.

SUMMARY OF THE INVENTION

The present invention seeks to overcome the disadvantages in the prior art and to provide a simpler and easier method for obtaining cardiac output by measuring the arterial pressure waveform and in turn providing measurement of cardiac output or total peripheral resistance.

According to the invention there is provided a method for deriving cardiac output in a patient including the steps of: measuring continuously the arterial pressure at a point within the cardiovascular system to derive an arterial pressure waveform; determining the mean arterial pressure from said arterial pressure waveform; determining the compliance of the arterial system for the patient; determining the time constant of the arterial system from the arterial pressure waveform and deriving the mean cardiac output as the product of the mean arterial pressure and compliance divided by said time constant.

The time constant of the arterial system corresponds to the time from the dicrotic notch to the time where the slope of the arterial pressure waveform at the dicrotic notch intersects the time axis, equivalent to extrapolation of the waveform to zero arterial pressure. The dicrotic notch corresponds to the pulse in the arterial pressure waveform produced by aortic valve closure. The arterial pressure waveform after the dicrotic notch can be represented by an exponential decay curve.

The compliance of the arterial system is obtained from a set of nomograms which are normalised and based on the weight, height, age and sex of a patient.

Other factors can be determined from these measurements including stroke volume which is the mean cardiac output divided by the heart rate. Cardiac contractility can be derived from the positive slope of the arterial pressure waveform, maximum contractility being taken from the steepest part of that slope which can then be displayed both as a rate of change of pressure or, when the stroke volume is known, as the rate of change of volume. Other determinations that can be provided by the current measurement techniques include the ejection period which is the interval from the commencement of the upswing of the arterial pressure waveform to the dicrotic notch.

Other parameters can also be determined from the above measurements, the explanation of which is made below.

BRIEF DESCRIPTION OF THE DRAWINGS

The present invention will now be described with respect to the following figures in which.

PREFERRED MODES FOR PERFORMING THE INVENTION

Figure 1:
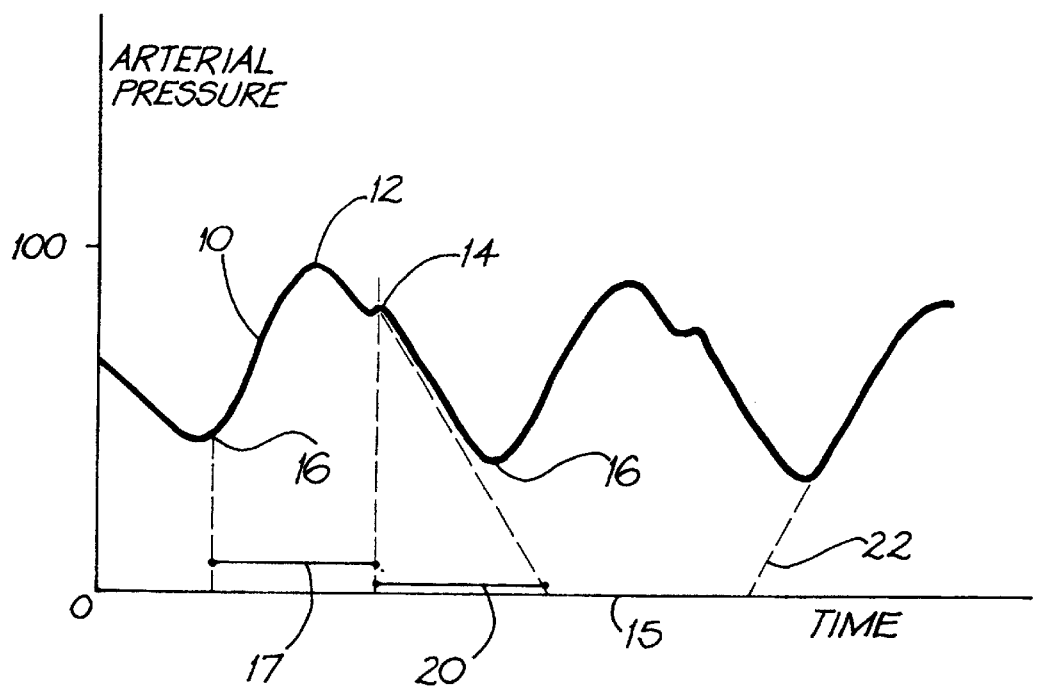
FIG. 1 shows the arterial pressure waveform of a patient plotted with respect to time measured at a peripheral location, for example in a finger of a patient.

As shown in FIG. 1, the arterial pressure waveform rises and falls with the activity of the heart, the upswing 10 corresponding to the contraction of the heart. This rises to a maximum known as the systolic blood pressure 12 and falls to a notch 14 called the dicrotic notch indicative of the closure of the aortic valve. As the pressure declines past the dicrotic notch 14 it reaches a minimum at 16 corresponding to the diastolic blood pressure, before contraction again of the heart muscle increases the blood pressure and the cycle repeats.

The period from the minimum point 16 in the curve to the next successive dicrotic notch 14 is known as the ejection period 17.

The arterial pressure waveform, as shown in FIG. 1, can be measured by a non invasive technique such as the Penaz technique described in U.S. Pat. No. 4,869,261. This method employs a cuff placed about the finger attached to a transducer to measure pressure and includes an air pump with a servocontrol valve allowing the cuff to be inflated. An infra red light emitting diode is also employed in combination with a photocell to act as a photoplethysmograph. The photocell measures absorption at an infra red wavelength appropriate for arterial blood and thus detects the volume of arterial blood in the finger under the cuff. This volume varies according to the degree of distention of the arteries during systole. An electronic processor analyses the photoplethysmograph to determine the volume at a point set according to the mean arterial pressure. Then the servocontrol valve at the air pump acts as a feed back mechanism continuously inflating or deflating the finger cuff in order to maintain the photoplethysmograph output constant at the said point. The pressure at the transducer consequently gives a continuous tracing of arterial pressure.

An alternative method for measuring the arterial pressure waveform non-invasively is to employ a pressure tonometer technique such as used in the apparatus sold as the SphygmoCorMx (trade mark) or SphygmoCorPx (trade mark) system.

The arterial pressure waveform can also be measured by an invasive technique such as employed for continuous monitoring of blood pressure. In this technique, a cannula, placed percutaneously in an artery, for example, the radial artery, is connected to a pressure transducer through a fluid filled non-compliant manometer line incorporating a continuous and intermittent flush device (see Hinds C J, Watson D "Intensive care: a concise textbook" W B Saunders 1996). The electrical output from the pressure transducer provides the arterial pressure waveform signal. The pressure transducer and manometer line are supplied in disposable sterile packages for immediate use and are supplied by such companies as Datex/Ohmeda, Abbott, Baxter, Beckton-Dickinson.

An invasive technique is more accurate than a non-invasive technique but in this technique a small error will occur if the time constant of the transducer and manometer lines is ignored. This error is in the region of 2%–5%. This error can be corrected for if the time constant is measured. Measuring involves pressurizing the manometer line at the arterial end, ensuring a stable reading from the pressure transducer and then recording the pressure drop which occurs with the sudden release in pressure at the arterial end of the manometer line. The time constant is then the tangent to the curve of the pressure drop. The time constant was found to be the same for pressures of 100 mm Hg, 200 mm Hg and 300 mm Hg covering the range of arterial pressures met in clinical practice. A Datex/Ohmeda system including transducer and manometer line was measured to have a time constant of 50 milliseconds. To correct for this error, the time constant for the pressure transducer and manometer line is subtracted from the time constant of the arterial system measured according to the invention as described herein.

Once the arterial pressure waveform has been measured various parameters can be derived therefrom in the following manner.

The mean arterial pressure can be obtained by integrating the arterial pressure waveform over a period of several seconds and averaging the result. In ill patients or patients under artificial respiration or ventilation, for example it has been found that cardiac output often varies from one heart beat to the next and averaging over a long enough interval is required to obtain a reliable measurement. A period of fifteen seconds is considered suitable for this purpose.

The compliance of the arterial system, that is the ability of the system to be able to respond elastically to given loads or inputs is relatively constant with respect to such factors as weight, height, age and sex. A table of such compliances can be determined for a population as a function of the weight, height, age and sex of a patient.

One method for determining the compliance is based on the following analysis. Normal blood volume may be taken as 85 ml. per kilogram body weight (SCHOLAR H. Am. Heart J. 1965, 69, 701). Reduction of these values by 10% should be made for obese subjects and the elderly (ALBERT S. N. Blood Volume. 1963). The percentage of the blood volume contained in the arterial system is 11% of the total blood volume, comprising 2% in the aorta, 8% in the arteries and 1% in the arterioles (WILLIAM F. GANONG. Review of Medical Physiology. $15^{th}$ edition p534.).

It has been found in healthy patients that the arterial system has an overall increase in size of 25% with a pressure rise of 100 mm.Hg. The aorta is very distensible, and shows the largest increase in volume compared to other components of the arterial system. While the arteries have more blood volume, they are less distensible (KELMAN G. R. Applied Cardiovascular Physiology 1971 p73.).

Blood pressure/volume relationships between the ages of 20 and 75 years show decreasing compliance with age which, although similar and fairly linear at low pressures, show large differences at higher pressures (JOSEPH BOYLE 111 $2^{nd}$ edition Physiology, NMS 1991 P93.)

Thus a basis for deriving arterial compliance for a patient is based on factors of weight, height, age and blood pressure. The sex of a patient may also be relevant. Nomograms and formulae for compliance based on the height and weight of a subject are available (NADLER, S. B. HIDALGO J. V. and BLOCH T. Surgery 1962 51224).

A basic compliance figure can be derived from the following calculation:

Assuming that the total blood volume is 85 millilitres per kilogram body weight and that 11% is in the arterial system gives a figure of 9.35 millilitres of blood per kilogram body weight in the arterial system; compliance for a 25% increase in arterial volume is 2.3375 ml/100 mm. Hg. pressure change; thus the base figure for computing compliance is 0.023375 ml./mm. Hg./kg. body weight.

For a 70 kilogram young healthy adult this would give a compliance of 1.63625 ml./mm.Hg.

A table of compliance can therefore be generated for factors such as age, height, and weight from which compliance can be determined.

After multiple cardiac output measurements have been checked by using this method simultaneously with other cardiac output monitors of existing design, statistical analysis will indicate the need for any correction factors. As mean arterial pressure and the time constant are both accurately measured, any correction will only apply to the compliance tables. This will then improve the accuracy of future cardiac output measurements.

Intra-arterial pressure measurements are preferred for accuracy but non-invasive methods using a derived calibrated arterial trace will be sufficiently accurate for the many clinical purposes where an intra-arterial line will not be justified. e.g. hospital outpatients or doctors consulting rooms.

For accuracy it is also necessary to correct the compliance for absent limbs, or during surgical procedures for periods when a tourniquet is applied to a limb or during surgical clamping of a major artery.

While compliance figures derived from the above method may be initially less accurate than desirable, the current method is of value in continuous monitoring as changes in cardiac output, or in total peripheral resistance rather than absolute values, per se, will be of great value. For example, in situations where blood loss, or fluid replacement, or the effect of drugs is being monitored such changes in cardiac output or total peripheral resistance will enable earlier corrections to be made.

An alternative method of obtaining the compliance of the arterial system is by measuring the pulse wave velocity. The rate of travel of a pulse wave is inversely proportioned to the compliance of a given system. So, for example, a non invasive tonometric measurement of the time interval between the carotid and femoral pulse waves may be used to determine pulse wave velocity and so derive compliance. A device for measuring the pulse wave velocity is sold as the SphygmoCor Vx system (trade mark) by PWV Medical Pty Ltd.

Immediately following the dicrotic notch, corresponding to the closure of the aortic valve, the arterial system becomes the electrical equivalent of a capacitive system with a resistive leak. The arterial vessels with their volume and elasticity provide the capacitance of the system while the flow through the small arterioles is the leakage volume through a resistance equivalent. The rate of drop of pressure in the arterial system is indicative of the slope of the arterial pressure waveform after the dicrotic notch 14. If the time interval from the dicrotic notch 14 to the time 15 at which the projection of this line intersects the point of zero arterial pressure on the pressure scale, that is , the intersection with the time axis, is measured then that time interval 20, as shown in FIG. 1, will correspond to the time constant of the arterial system.

Using these determinants of mean arterial pressure, compliance and time constant, it is possible to calculate the cardiac output by first calculating the total peripheral resistance since the product of compliance and total peripheral resistance equals the time constant 20 determined for the system. The calculated total peripheral resistance can then be used with the measured mean arterial pressure to calculate the mean cardiac output. The mean cardiac output is the mean arterial pressure divided by the total peripheral resistance. That is, mean cardiac output is equal to the product of mean arterial pressure and compliance divided by the time constant.

Having determined the mean cardiac output, the stroke volume is the mean cardiac output divided by the heart rate. The heart rate is the inverse of the period of the arterial pressure waveform, that is, the inverse of the time between successive times of the waveform, for example times 12 of systole, which can be measured from the arterial pressure waveform. The maximum cardiac contractility is derived from the maximum 22 of the upswing 10 of the arterial pressure waveform which can then be displayed either as a rate of change of pressure or, if stroke volume has been calculated, as the rate of change of volume.

The cardiac index can be derived as this relates the cardiac output to the body surface area based on an existing formula relating height and weight of a patient. One further parameter which may be useful to display is the systolic pre-ejection period which is the period from the commencement of the ventricular activity until the commencement of the pressure rise. The ventricular electrical activity can be measured with an electrocardiograph. Because there is a delay in the pulse signal travelling from the heart to the transducer, a microphone can be used over the aortic valve to give a signal corresponding to the sound of the aortic valve closing, which signal will be marginally ahead of the displayed dicrotic notch, to allow a correction for the accurate determination of this action in time.

The role of the new system will be of value as an indication from moment to moment of changes in cardiac output and peripheral resistance. Any changes associated with blood loss or fluid replacement will be seen as will be changes associated with the administration of any anaesthetic agents or other drugs. Achieving adequate peripheral perfusion will be greatly facilitated and the method could play a role in patient management in intensive care as well as in the operating theatre. The method has application in accident and emergency units as well as in general wards. It is assumed that an individual's arterial compliance does not change greatly over a small period of time although it does change gradually over the years and hence once this has been determined, the parameters displayed by a patient are easy to identify from a given starting base, making dysfunction more readily determinable.

It is also contemplated that the method could have application in veterinary practices where suitable management of arterial pressure can be made.

The apparatus for determining these factors can be made portable making it useful for on site emergency procedures or for at home patient care.

Any micro controller or micro computer well known to the technician in the field of electronics or medical electronics can be used as a programmable device to measure and calculate the above stated parameters. Compliance tables can be provided in a ROM chip or, if compliance values are to be upgradeable in an EEPROM or a Read Mostly Memory (RMM chip) and the arterial pressure can be measured by a transducer with the values inputted to the microprocessor or microcontroller after conversion to a digital form. The hardware and software components are well known in the art and it is within the skill of a person of average ability in the art to construct a device to determine these parameters or write software to operate the microcontroller or microprocessor to perform these functions.

Figure 2:
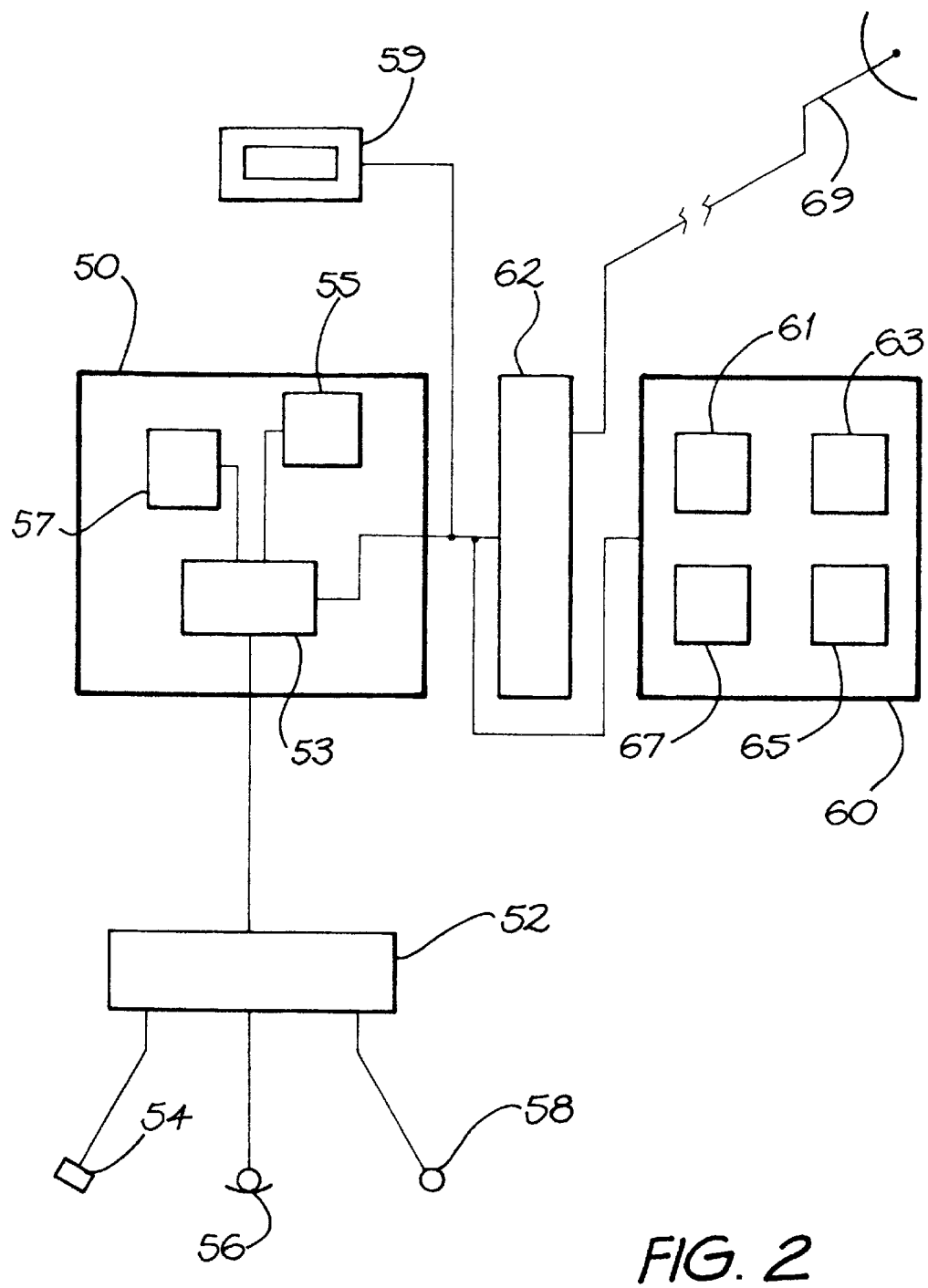
FIG. 2 shows a block diagram of an apparatus for performing the method according to the invention.

For example, as shown in FIG. 2, a typical apparatus involves a computer 50 having an input 52 from sensors 54, 56, 58 corresponding respectively to an arterial pressure waveform transducer, an acoustic transducer and one or more electrocardiographic leads. The computer 50 involves a processing unit 53 operated under software control in RAM 55 or ROM 57 which performs a series of software steps such as set forth in FIG. 3. The output of these software steps provides values which can be displayed as tables 61, 63, 65, 67 in an output device 60 such as a visual display unit, a cathode ray tube, a meter or similar device, a printer 59, or may be input into a further communication device 62 for transmission to a remote location either over a phone line or via wireless link, 69, including radio, optical fibre, microwave link or the like. A meter may be an electromechanical device or may be a light emitting diode display or a liquid crystal display.

Figure 3:
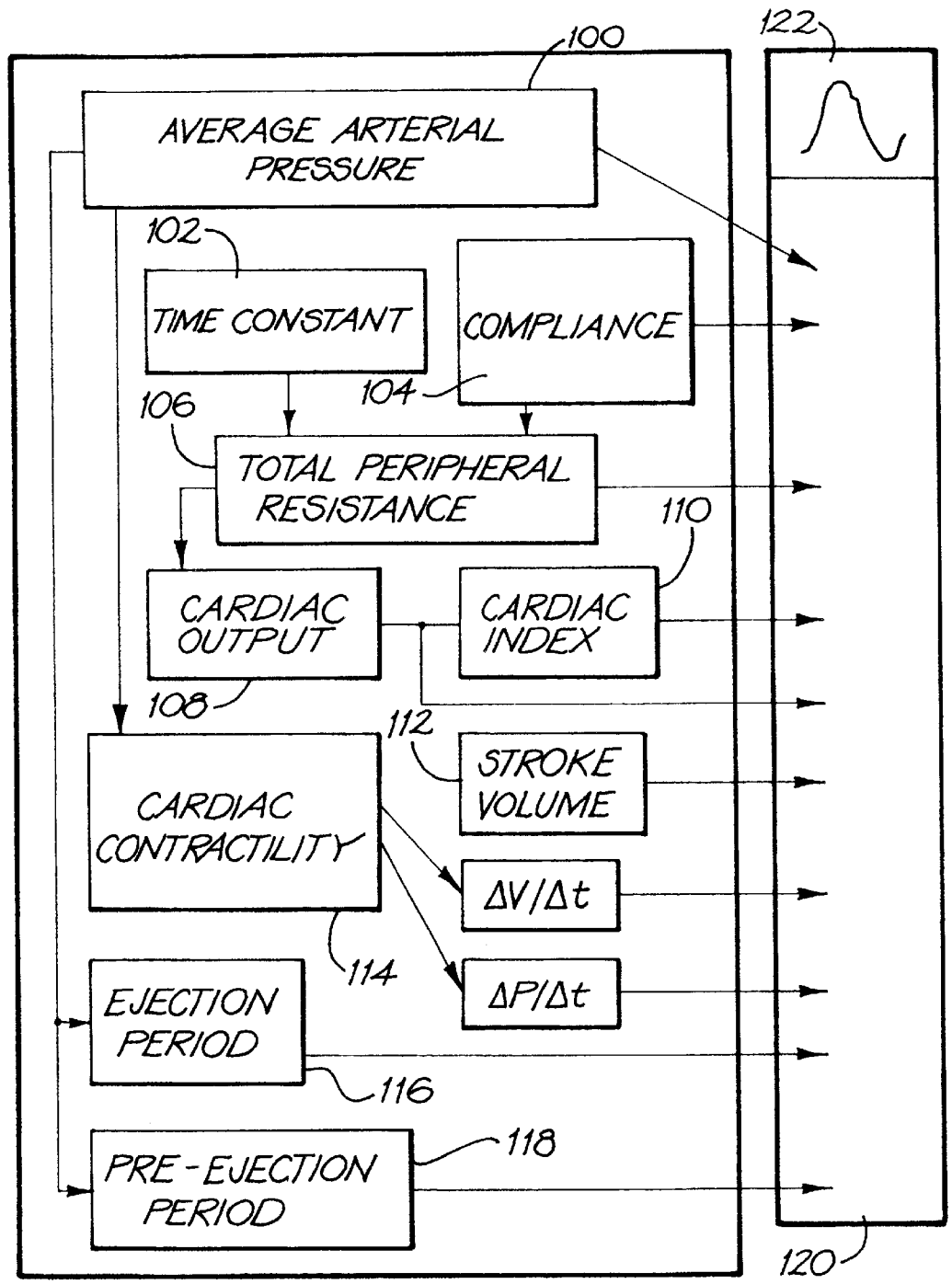
FIG. 3 shows a flow chart for the apparatus of FIG. 2 for providing the values that can be determined according to the invention.

Referring to FIG. 3, the series of software steps perform the following operations. The peripheral arterial pressure trace is input through the input device as discussed above. The trace may be converted from an analogue form to a digital form for processing by the computer if it is a digital computer. It is also contemplated that the various calculations and outputs can be performed using an analogue computer although this is less preferred.

Once the trace has been converted to a digital form, the trace is sampled over a period of typically 15 seconds and averaged to provide the average arterial pressure (step 100).

The time constant is calculated by analysing the slope of the trace at the dicrotic notch and extrapolating this slope to zero pressure (step 102). When the aortic valve closes the arterial pressure waveform includes noise components due thereto. Measurement of the slope is therefore delayed to minimise the effect of such noise and is sampled a number of times every millisecond after valve closure to determine the reliability of the measurement. In addition the slope is then averaged for a number, for example 15, heartbeats. The computer has available a table of compliances, for example, stored in ROM device 57, derived, as discussed above, from a series of nomograms or derived from a pulse wave velocity technique determined concurrently with the arterial pressure waveform (step 104). The time constant is divided by the compliance to determine the total peripheral resistance (step 106). The total peripheral resistance can then be used with the mean arterial pressure to determine the cardiac output (step 108). The cardiac output can then be used to determine a variety of subsequent values including the cardiac index (step 110) and the stroke volume (step 112).

From the arterial pressure trace the maximum slope of the upswing of the arterial pressure wave from the start of systole provides contractility (step 114). The stroke volume can be used to then express the cardiac contractility as a rate of change in volume.

Calculation of the period from the start of the upswing in the arterial pressure waveform until the dicrotic notch provides the ejection period in seconds ( step 116).

Combining the arterial pressure waveform with an ECG input from the input 58 and the microphone 56 located over the aorta (to detect closure of the aortic valve) can be used to derive the pre-ejection period (step 118).

The outputs from these calculations or steps can then be displayed in a tabular, or numerical or histographic form 120 for interpretation while the arterial pressure waveform is displayed as an analogue trace 122. The display of output values 120 may, for example include the values of: systolic pressure, diastolic pressure, heart rate, mean arterial pressure, compliance, total peripheral resistance, cardiac output, cardiac index, stroke volume, maximum contractility (expressed as volume and/or pressure change), ejection period and pre-ejection period.

Alternatively, these values may be transmitted to a remote location through a telecommunications link 69 for evaluation by a specialist, for example, in a road side emergency or in a home care environment.

It is not considered necessary to include the exact sequence of steps for calculating the various values in the flow diagram shown with respect to FIG. 3 as this is within the skill of an average programmer or workman in the field.

The foregoing description has been limited to specific embodiments of this invention. It will be apparent, however, that variations and modifications may be made to the invention, with the attainment of some or all of the advantages of the invention. For example, some other technique other than the Penaz method, PWV Medical's method or an invasive method using a catheter in the radial artery may be used to determine the arterial pressure waveform, or it will be appreciated that the invention may be embodied in either hardware or software in a suitably programmed digital data processing system, both of which are readily accomplished by those of ordinary skill in the respective arts. Therefore, it is the object of the appended claims to cover all such variations and modifications as come within the true spirit and scope of the invention.

What is claimed is:

1. A method for deriving cardiac output in a patient comprising the steps of:
    measuring continuously the arterial pressure at a point within the cardiovascular system to derive an arterial pressure waveform;
    determining the mean arterial pressure from said arterial pressure waveform;
    determining the compliance of the arterial system for the patient;
    determining the time constant of the arterial system from the arterial pressure waveform and deriving the mean cardiac output as the product of the mean arterial pressure and compliance divided by said time constant.

2. A method for deriving a cardiac output in a patient as claimed in claim 1 wherein said step of determining compliance is determined from a table expressing compliance as a function of weight, height, age and sex of the patient.

3. A method for deriving cardiac output in a patient as claimed in claim 2 wherein said time constant is the rate of change of the arterial pressure waveform substantially after the dicrotic notch.

4. A method for deriving cardiac output in a patient as claimed in claim 3 wherein said rate of change is the slope of the arterial pressure waveform after the dicrotic notch extrapolated to zero arterial pressure.

5. A method for deriving cardiac output in a patient as claimed in claim 4 further including the step of measuring heart rate and calculating stroke volume by dividing said mean cardiac output by said heart rate.

6. A method for deriving cardiac output in a patient as claimed in claim 5 wherein said step of measuring heart rate includes measuring the pulse period of said arterial pressure waveform and taking the inverse thereof.

7. A method for deriving cardiac output in a patient as claimed in claim 6 wherein said step of measuring continuously the arterial pressure includes using a finger cuff transducer.

8. A method for deriving cardiac output in a patient as claimed in claim 6 wherein said step of measuring continuously the arterial pressure includes using a pressure tonometer.

9. A method for deriving cardiac output in a patient as claimed in claim 6 wherein said step of continuously measuring the arterial pressure includes using an intra-arterial catheter and pressure transducer.

10. A method for deriving cardiac output in a patient as claimed in claim 1 wherein said step of determining compliance is determined by measuring pulse wave velocity.

11. A method for deriving cardiac output in a patient as claimed in claim 10 wherein said step of measuring continuously the arterial pressure includes using a finger cuff transducer.

12. A method for deriving cardiac output in a patient as claimed in claim 10 wherein said step of continuously measuring the arterial pressure includes using a pressure tonometer.

13. A method for deriving cardiac output in a patient as claimed in claim 10 wherein said step of continuously measuring the arterial pressure includes using an intra-arterial catheter and pressure transducer.

14. An apparatus for deriving cardiac output in a patient including means for continuously measuring arterial pressure at a point within the cardiovascular system; means for processing said measured arterial pressure including means for calculating the mean arterial pressure; means for inputting compliance values; and means for measuring the time constant of the arterial system from said measured arterial pressure; and means for calculating cardiac output as the product of mean arterial pressure and compliance divided by said time constant, and further including means for displaying at least said arterial pressure and said cardiac output.

15. An apparatus for deriving cardiac output in a patient as claimed in claim 14 wherein said means for calculating said mean arterial pressure and said cardiac output includes a digital computer.

16. An apparatus for deriving cardiac output in a patient as claimed in claim 15 wherein said compliance values are stored in a memory device connected to said digital computer.

17. An apparatus for deriving cardiac output in a patient as claimed in claim 16 wherein said means for displaying includes means for displaying said arterial pressure and said cardiac output remotely from said means for continuously measuring said arterial pressure.

18. An apparatus for deriving cardiac output in a patient as claimed in claim 17 further including means for acoustically determining aortic valve closure.

19. An apparatus for deriving cardiac output in a patient as claimed in claim 18 further including means for measuring the electrical activity of the heart.

20. An apparatus for deriving cardiac output in a patient as claimed in claim 19 wherein said means for acoustically determining aortic valve closure and said means for measuring the electrical activity of the heart include respectively a microphone and an electrocardiograph.

21. An apparatus for deriving cardiac output in a patient as claimed in claim 15 wherein said means for continuously measuring arterial pressure at a point within the cardiovascular system includes a finger cuff transducer.

22. An apparatus for deriving cardiac output in a patient as claimed in claim 15 wherein said means for continuously measuring arterial pressure at a point within the cardiovascular system includes a pressure tonometer.

23. An apparatus for deriving cardiac output in a patient as claimed in claim 15 wherein said means for continuously measuring arterial pressure at a point within the cardiovascular system includes an intra-arterial catheter and pressure transducer arrangement.

24. A method for deriving cardiac output comprising the steps of:

measuring continuously a patient's arterial pressure at a point within the patient's cardiovascular system for deriving an arterial pressure waveform;

determining compliance of the patient's arterial system;

determining a time constant of the patient's arterial system from the arterial pressure waveform and deriving peripheral resistance as said time constant divided by said compliance; and, determining mean arterial pressure from said arterial pressure waveform and deriving mean cardiac output as a product of said peripheral resistance and said mean arterial pressure.

25. A method for deriving cardiac output comprising the steps of:

measuring continuously a patient's arterial pressure at a point within the patient's cardiovascular system for deriving an arterial pressure waveform;

determining the compliance of the patient's arterial system; and, determining a time constant of the patient's arterial system from the arterial pressure waveform and deriving peripheral resistance as said time constant divided by said compliance.

\* \* \* \* \*

UNITED STATES PATENT AND TRADEMARK OFFICE
CERTIFICATE OF CORRECTION

PATENT NO. : 6,485,431 B1  Page 1 of 1
DATED : November 26, 2002
INVENTOR(S) : Duncan Campbell It is certified that error appears in the above-identified patent and that said Letters Patent is hereby corrected as shown below:

<u>Title page,</u>
Item [73], Assignee, please add:
-- Duncan Campbell Patents Pty. Ltd., Beecroft (AU)
  and
  John Uhlir, Abbotsford (AU) --

Signed and Sealed this

Eleventh Day of May, 2004

JON W. DUDAS
*Acting Director of the United States Patent and Trademark Office*